United States Patent
Anraku et al.

(10) Patent No.: US 9,804,198 B2
(45) Date of Patent: Oct. 31, 2017

(54) ALLOY MATERIAL, CONTACT PROBE, AND CONNECTION TERMINAL

(71) Applicants: Yamamoto Precious Metal Co., Ltd., Osaka-shi (JP); Shinko Metal Products Co., Ltd., Kitakyushu-shi (JP); NHK Spring Co., Ltd., Yokohama-shi (JP)

(72) Inventors: Teruo Anraku, Osaka (JP); Masayuki Ainoya, Kochi (JP); Tomohiro Kubota, Kochi (JP); Kotaro Toyotake, Fukuoka (JP); Tomoyuki Minami, Fukuoka (JP); Noritoshi Takamura, Kanagawa (JP); Humio Takahashi, Kanagawa (JP)

(73) Assignees: Yamamoto Precious Metal Co., Ltd., Osaka-shi (JP); Shinko Metal Products Co., Ltd., Kitakyushu-shi (JP); NHK Spring Co., Ltd., Yokohama-shi (JP)

( * ) Notice: Subject to any disclaimer, the term of this patent is extended or adjusted under 35 U.S.C. 154(b) by 150 days.

(21) Appl. No.: 14/418,964

(22) PCT Filed: Aug. 2, 2013

(86) PCT No.: PCT/JP2013/071076
§ 371 (c)(1),
(2) Date: Feb. 2, 2015

(87) PCT Pub. No.: WO2014/021465
PCT Pub. Date: Feb. 6, 2014

(65) Prior Publication Data
US 2015/0168455 A1 Jun. 18, 2015

(30) Foreign Application Priority Data
Aug. 3, 2012 (JP) ................................. 2012-172987

(51) Int. Cl.
*G01R 31/20* (2006.01)
*G01R 1/073* (2006.01)
(Continued)

(52) U.S. Cl.
CPC ................ *G01R 1/073* (2013.01); *C22C 5/04* (2013.01); *C22C 30/02* (2013.01);
(Continued)

(58) Field of Classification Search
CPC ........ B01J 2/00; H01L 21/00; H01L 2221/00; C12Q 1/00; C12Q 2304/00
See application file for complete search history.

(56) References Cited

U.S. PATENT DOCUMENTS 4,254,548 A * 3/1981 Arakawa ............. H01L 21/4871
148/516
5,833,774 A 11/1998 Klein et al.
(Continued)

FOREIGN PATENT DOCUMENTS

JP 59-179740 A 10/1984
JP 60-131716 A 7/1985
(Continued)

OTHER PUBLICATIONS

Supplementary European Search Report dated Mar. 24, 2016, issued for the corresponding European Patent Application No. 13825678.9.
(Continued)

*Primary Examiner* — Jermele M Hollington
*Assistant Examiner* — Temilade Rhodes-Vivour
(74) *Attorney, Agent, or Firm* — Locke Lord LLP

(57) ABSTRACT

An alloy material includes: a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and at least one of manganese (Mn), tin (Sn), silicon (Si), antimony (Sb),
(Continued)

titanium (Ti) and magnesium (Mg) added to the composition in a range of 4.5 at % or less, and the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition.

10 Claims, 6 Drawing Sheets

(51) Int. Cl.
    *C22C 5/04*     (2006.01)
    *C22C 30/02*     (2006.01)
    *G01R 1/067*     (2006.01)
    *G01R 3/00*     (2006.01)
    *G01R 31/28*     (2006.01)
    *B01J 2/00*     (2006.01)
    *C12Q 1/00*     (2006.01)

(52) U.S. Cl.
    CPC ........... *G01R 1/06722* (2013.01); *G01R 3/00* (2013.01); *G01R 31/2886* (2013.01); *B01J 2/00* (2013.01); *C12Q 1/00* (2013.01); *H01L 2221/00* (2013.01)

(56) References Cited

U.S. PATENT DOCUMENTS

| | | | |
|---|---|---|---|
| 8,183,877 B2 | 5/2012 | Tanaka | |
| 8,310,254 B2 | 11/2012 | Morita et al. | |
| 2011/0048962 A1* | 3/2011 | Reece | C25B 1/04 205/633 |
| 2012/0187000 A1* | 7/2012 | Kahn | G01N 27/3335 205/782 |
| 2012/0231972 A1* | 9/2012 | Golyshin | C12Q 1/00 506/11 |
| 2013/0271173 A1* | 10/2013 | Obata | C22C 5/00 324/755.11 |
| 2014/0377129 A1* | 12/2014 | Shishino | C22C 30/02 420/587 |

FOREIGN PATENT DOCUMENTS

| | | |
|---|---|---|
| JP | 60-131779 A | 7/1985 |
| JP | 60-159140 A | 8/1985 |
| JP | 2004-093355 A | 3/2004 |
| JP | 4176133 B1 | 11/2008 |
| JP | 4216823 B2 | 1/2009 |
| JP | 2011-122194 A | 6/2011 |
| JP | 4878401 B1 | 2/2012 |
| TW | 201229519 A | 7/2012 |
| WO | 2009/102030 A1 | 8/2009 |
| WO | 2012/067126 A1 | 5/2012 |
| WO | WO-2012/077378 A1 | 6/2012 |

OTHER PUBLICATIONS

Office Action dated Dec. 27, 2014, issued for the Taiwan Application No. 102127928.
International Search Report dated Oct. 29, 2013, issued for PCT/JP2013/071076.
Office Action dated May 9, 2017 in the corresponding Japanese application No. 2014-528246 and machine English translation thereof.

* cited by examiner

ALLOY MATERIAL, CONTACT PROBE, AND CONNECTION TERMINAL

FIELD

The present invention relates to, for example, an alloy material; and also to a contact probe used for a continuity test or a performance test of a test target such as a semiconductor integrated circuit, and a liquid crystal panel, and a connection terminal connecting electrical contacts with each other, which consist of the alloy material.

BACKGROUND

Conventionally, when a continuity test or a performance test of a test target such as a semiconductor integrated circuit, and a liquid crystal panel is performed, a conductive contact probe providing the electrical connection between a test target and a signal processor having a semiconductor integrated circuit that outputs signals for testing is used. In order to perform an accurate continuity test or performance test, it is required to reliably perform the input and output of signals for testing through a contact probe. Herein, a contact probe repeatedly contacts with a test target such as a semiconductor integrated circuit and a liquid crystal display, and an electrical testing or measurement is performed. At that time, for example, when the contact probe is oxidized by the repeated use, the test results are affected.

Therefore, for the material used in a contact probe, high conductivity and corrosion resistance, and favorable oxidation resistance are required. For this requirement, in order to improve the oxidation resistance, for example, it can be mentioned to use a material in which tool steel has been plated with Au, however, the plating film is peeled off, and the background skin of the tool steel is exposed, as a result, the electric resistance is increased when the exposed material is contacted with a test target. Further, due to the exposure of the background skin of the tool steel, there may be a case where the background skin adheres to a test target as a foreign matter, and causes continuity failure. In order to eliminate the continuity failure, in the material to be used, it is most important to have the properties of low electric resistance and hardly-worn high hardness to suppress the wear of the contact probe itself even if the contact with a test target is performed in a repeated testing.

Among the materials having a property of high hardness, a copper (Cu)-beryllium (Be) alloy and a tungsten wire are mentioned as the metal material, however, are poor in the oxidation resistance to be used as a contact probe. A Cu—Be alloy, a tungsten wire, or the like in which metals other than noble metals are contained in large amount have high hardness, however, have a nature susceptible to oxidation, and when oxidation is caused, the conductivity is deteriorated, and the stable testing measurements cannot be performed. Therefore, an alloy having excellent oxidation resistance and conductivity, capable of being used for a long time, and having high conductivity, in which any of gold (Au), silver(Ag), platinum (Pt), palladium (Pd), and Cu is used as a main component, is used (see, for example, Patent Literatures 1 to 5).

CITATION LIST

Patent Literature

Patent Literature 1: Japanese Patent No. 4878401
Patent Literature 2: Japanese Patent No. 4176133
Patent Literature 3: Japanese Patent No. 4216823
Patent Literature 4: Japanese Laid-open Patent Publication No. 2004-93355
Patent Literature 5: Japanese Laid-open Patent Publication No. 2011-122194

SUMMARY

Technical Problem

However, in an alloy in which Pt is used as a main component, there may be a case where the workability of an extra fine wire or a thin plate is poor. Further, an alloy in which Au is used as a main component is excellent in the workability, however, the improvement of Vickers hardness by age hardening is hardly obtained, therefore, the alloy is not suitable for use in a contact probe. Furthermore, an alloy in which Pd is used as a main component is more stable in the workability as compared with the alloy in which Pt or Au is used as a main component, however, there may be a case where the intended hardness is not obtained by age hardening depending on the composition ratio or the kind of the additional metal.

The present invention has been made in view of the above, and an object of the present invention is to provide an alloy material having excellent conductivity, and further having high hardness and excellent workability; and a contact probe and a connection terminal each of which consists of the alloy material.

Solution to Problem

To solve the above-described problem and achieve the object, an alloy material according to the present invention includes: a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and at least one of manganese (Mn), tin (Sn), silicon (Si), antimony (Sb), titanium (Ti) and magnesium (Mg) added to the composition in a range of 4.5 at % or less, wherein the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition.

Moreover, the alloy material according to the present invention further includes one of iridium (Ir), ruthenium (Ru) and a combination of Ir and Ru added in an amount of 0.01 at % to 0.05 at %.

Moreover, in the alloy material according to the present invention, Vickers hardness is HV 480 to 560 after heating at 300° C. to 450° C. and aging.

Moreover, a conductive contact probe according to the present invention contacts with each of contact targets at both ends in a longitudinal direction, and at least part of which is formed using the alloy material according to the above-described invention.

Moreover, the conductive contact probe according to the present invention includes: a first conductive plunger contacting with one of contact targets at one end; a second conductive plunger contacting with other one of the contact targets at the other end; and a coil spring arranged between the first plunger and the second plunger so as to elastically connect the first and the second plungers with each other, wherein at least one of the first plunger, the second plunger, and the coil spring consists of the alloy material according to the above.

Moreover, a conductive connection terminal according to the present invention contacts with each of contact targets at both ends in a longitudinal direction, and at least part of which is formed using the alloy material according to the above-described invention.

Advantageous Effects of Invention

According to the present invention, in a composition range of a ternary alloy of Ag, Pd, and Cu, composition contains 17 at % to 25 at % of Ag, 30 at % to 45 at % of Pd, and 30 at % to 53 at % of Cu are contained as composition, and at least one of Mn, Sn, Si, Sb, Ti, and Mg is added based on the composition, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at %, respectively, therefore, an effect in which an alloy material having excellent conductivity, and further having high hardness and excellent workability for use in a contact probe or a connection terminal can be obtained is exerted.

DESCRIPTION OF EMBODIMENTS

Figure 1:
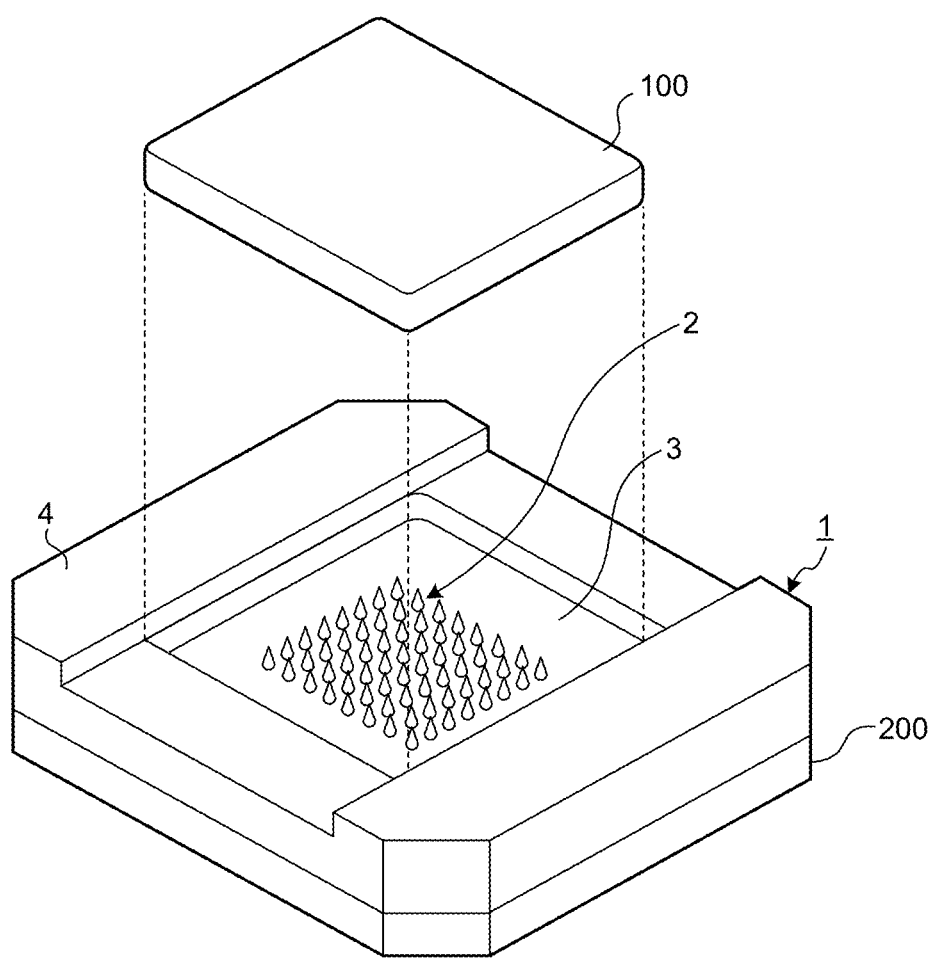
FIG. 1 is a perspective view illustrating a schematic configuration of a socket according to one use mode of an alloy material in an embodiment of the present invention.

Hereinafter, the embodiment for carrying out the present invention will be explained in detail with the drawings. However, the present invention should not be construed to be limited to the following embodiments. Further, each of the drawings to be referred in the following explanation only roughly illustrates the shape, size, and positional relationship in a degree such that the contents of the present invention can be understood. That is, the present invention is not limited to only the shape, size, and positional relationship illustrated in each of the drawings.

The alloy material according to the embodiment of the present invention will be explained. The alloy material according to the embodiment contains a ternary alloy of Ag—Pd—Cu. The ternary alloy of Ag—Pd—Cu according to the embodiment is an alloy formed in a range of 17 at % Ag-30 at % Pd-53 at % Cu, 25 at % Ag-30 at % Pd-45 at % Cu, 17 at % Ag-45 at % Pd-38 at % Cu, or 25 at % Ag-45 at % Pd-30 at % Cu. When the alloy composition is in such an atomic ratio, spinodal decomposition in which two phases of $\alpha_2$ (Ag) that is an Ag-rich phase, and β of PdCu appear occurs by aging treatment at the vicinity of 400° C., and also for the purpose of not mixing other appeared phases as much as possible, the alloy composition in such an atomic ratio is preferred. From also these reasons, the composition range of a ternary alloy of Ag—Pd—Cu is required to be limited in order to satisfy the improvement of the hardness by the two phases of appeared phases.

An alloy of Ag—Pd—Cu forms a phase of face-centered cubic (FCC) by the melting of Ag, Pd, and Cu together with one another in a high temperature range. Herein, Ag and Pd have a nature of melting together with each other in a high temperature range and also in a low temperature range. Further, Pd and Cu are involved in the hardening by melting with each other in a high temperature range and forming a β-phase that is a compound phase at the vicinity of 400° C., and in this case, the Vickers hardness is at most around HV 250. Ag and Cu have a nature of melting with each other in a high temperature range, however, in a low temperature range, separating into a Cu-rich phase $\alpha_1$ (Cu) and $\alpha_2$ (Ag). In a specific composition range of the ternary alloy, various phases appear, and in many cases, sufficient hardness is not obtained.

For example, in the composition of 20 at % Ag-25 at % Pd-55 at % Cu, when the aging treatment is performed at the vicinity of 400° C., two phases of $\alpha_1$ (Cu), and $\alpha_2$ (Ag) appear. Further, in the composition of 22 at % Ag-55 at % Pd-23 at % Cu, three phases of $\alpha_2$ (Ag), $\alpha_2$ (Pd) that is a palladium rich phase, and β appear. These appeared phases affect the Vickers hardness, in particular, when the appearance amount of $\alpha_1$ (Cu) or $\alpha_2$ (Pd) becomes large, the improvement of the Vickers hardness after aging treatment is hardly obtained.

Herein, in some composition ranges in which an atomic ratio of Pd is low and an atomic ratio of Cu is high, $\alpha_1$ (Cu) appears, however, the appearance amount is slight, therefore, the hardness is not largely affected. Further, in order to obtain the improved, maximum Vickers hardness, in a composition range of a ternary alloy of Ag—Pd—Cu of the alloy material according to the embodiment described above, it is preferable in a range of 18 at % Ag-35 at % Pd-47 at % Cu, 22 at % Ag-35 at % Pd-43 at % Cu, 18 at % Ag-40 at % Pd-42 at % Cu, or 22 at % Ag-40 at % Pd-38 at % Cu.

Further, in the alloy material according to the present embodiment, at least one of Mn, Sn, Si, Sb, Ti, and Mg is added in a range of 4.5 at % or less based on the composition in the composition range of a ternary alloy of Ag—Pd—Cu described above. Furthermore, each element is added respectively in a range of 0.5 at % to 3.5 at % of Mn, 1 at % to 2 at % of Sn, 0.5 at % to 2 at % of Si, 0.5 at % to 3 at % of Sb, 0.5 at % to 2 at % of Ti, and 0.5 at % to 3.5 at % of Mg. As a result, the Vickers hardness after aging treatment can be increased to HV 480 to 560.

On the contrary, when at least any one of Mn, Sn, Si, Sb, Ti, and Mg is not added based on the ternary alloy of Ag—Pd—Cu in a composition range described above, the improvement of Vickers hardness is not obtained.

Further, when into the alloy material with the composition described above, one of Ir and Ru is further added, or Ir and Ru are further added in combination in an amount of 0.01 at % to 0.05 at %, an alloy material having a Vickers hardness of HV 480 to 560 with favorable workability can be obtained.

According to the embodiment described above, in a composition range of a ternary alloy of Ag, Pd, and Cu, 17 at % to 25 at % of Ag, 30 at % to 45 at % of Pd, and 30 at % to 53 at % of Cu are contained as composition, and at least one of Mn, Sn, Si, Sb, Ti and Mg is added in a range of 4.5 at % or less based on the composition, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at %, respectively, therefore, an alloy material having excellent conductivity, and further having high hardness and excellent workability for use in a contact probe can be obtained.

Further, according to the present embodiment, in a ternary alloy of Ag—Pd—Cu based on Ag, Pd, and Cu, an additional metal for ensuring the Vickers hardness and the conductivity as a contact probe for a semiconductor testing apparatus to the ternary alloy can be found.

In the ternary alloy of Ag—Pd—Cu, difference is observed in the age hardening depending on the difference of phase transformation in a composition range, however, by the alloy material according to the present embodiment, the composition balance having a maximum of hardening effect is tried to be achieved by the composition in a range of 17 at % to 25 at % of Ag, 30 at % to 45 at % of Pd, and 30 at % to 53 at % of Cu in a composition range.

Herein, Pd and Cu form a compound phase and harden, and the limit of the hardness is around HV 250 in the maximum. On the contrary, when Ag is contained in an adequate amount, an $\alpha_2$ (Ag) phase and a $\beta$ phase can finely be separated to the maximum extent by age hardening. As a result, the Vickers hardness can be increased.

Further, according to the present embodiment, in the atomic ratio, based on the ternary alloy of Ag—Pd—Cu consisting of 17 at % to 25 at % of Ag, 30 at % to 45 at % of Pd, and 30 at % to 53 at % of Cu, at least one of Mn, Sn, Si, Sb, Ti and Mg is added in a range of 4.5 at % or less, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at % are added respectively, as a result, the Vickers hardness of the aged material heated at 300° C. to 450° C. and aging treated is HV 480 to 560, therefore, the wear resistance is improved as an alloy material, and the material becomes suitable for a material of an apparatus for semiconductor testing.

Further, according to the present embodiment, Ag and Cu tend to reduce the resistivity, and Pd tends to increase the resistivity and the oxidation resistance. That is, in the alloy material according to the present embodiment, the composition balance having conductivity and oxidation resistance is tried to be achieved while ensuring the property of high hardness.

As to the ratio relating to the alloy material of the present embodiment, based on the ternary alloy of Ag—Pd—Cu in a range of 17 at % Ag-30 at % Pd-53 at % Cu, 25 at % Ag-30 at % Pd-45 at % Cu, 17 at % Ag-45 at % Pd-38 at % Cu, or 25 at % Ag-45 at % Pd-30 at % Cu to satisfy the high hardness, at least one of Mn, Sn, Si, Sb, Ti and Mg is added in a range of 4.5 at % or less, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at %, respectively, as a result, the Vickers hardness after the heating at 300° C. to 450° C. and the aging treatment reaches HV 480 to 560. Even if in the composition outside the range of the ternary alloy of Ag—Pd—Cu, the addition is performed, the improvement of hardness is hardly obtained.

Further, as to the addition to the ternary alloy of Ag—Pd—Cu, even in the combination addition of Mn, Sn, Si, Sb, Ti, and Mg, the hardness is improved, however, the independent addition of Mn, Sn, Si, Sb, Ti, or Mg is more effective than the combination addition, and thus is preferred.

Furthermore, in a case where Mn is less than 0.5 at %, Sn is less than 1 at %, Si is less than 0.5 at %, Sb is less than 0.5 at %, Ti is less than 0.5 at %, or Mg is less than 0.5 at %, the improvement of the hardness is small. On the other hand, in a case where Mn exceeds 3.5 at %, Sn exceeds 2 at %, Si exceeds 2 at %, Sb exceeds 3 at %, Ti exceeds 2 at %, or Mg exceeds 3.5 at %, the workability is significantly deteriorated. Therefore, it is suitable to add the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at %.

Further, when the Mn, Sn, Si, Sb, Ti, and Mg in combination exceed 4.5 at %, the workability is deteriorated, therefore, the combination is not preferable. As to the Vickers hardness, the cast one is subjected to solution treatment at 850° C., and heated at 300° C. to 450° C., as a result, exerted the age hardening. In the age hardening at lower than 300° C., the improvement of hardness is hardly obtained, and in the age hardening at a temperature higher than 450° C., the hardness easily tends to be lowered, therefore, the temperature range described above is appropriate.

In the alloy material according to the present embodiment, any one of Ir and Ru can further be added, or Ir and Ru can further be added in combination, in an amount of 0.01 at % to 0.05 at %. These additional metals are useful for the workability, fine cracks on the surface of alloy are decreased during rolling and the workability is improved as compared with the one to which any additional metals have not been added. If the addition amount of the one of Ir and Ru, or the Ir and Ru in combination is 0.05 at % or more, the effect remains unchanged, therefore, 0.05 at % is an adequate amount. The Ir and Ru have action to micronize crystal grains, and if the crystal grains are small, intergranular cracks hardly occur during rolling.

Further, the alloy material according to the present embodiment has a material cost lower than that of the alloy in which Pt and Au are used as a main component.

Next, the case where the alloy material according to the present embodiment is used as a contact probe will be explained. FIG. 1 is a perspective view illustrating a schematic configuration of a socket (contact probe) according to one use mode of an alloy material in an embodiment of the present invention. Socket 1 illustrated in FIG. 1 is an apparatus used when electric characteristic testing of a semiconductor integrated circuit 100 that is a test target is performed, in which the semiconductor integrated circuit 100 is electrically connected with a circuit board 200 that outputs signals for testing to the semiconductor integrated circuit 100.

Socket 1 has multiple contact probes 2 (hereinafter, simply referred to as "probes 2") that is contact with one electrode (object to be contacted) of a semiconductor integrated circuit 100 that is a body to be contacted at one end side in the longitudinal direction, and contact with an electrode (object to be contacted) of a circuit board 200 at the other end side in the longitudinal direction, respectively; a probe holder 3 housing and holding multiple probes 2 in accordance with a predetermined pattern; and a holder member 4 that is provided around the probe holder 3, and suppresses the generation of positional displacement of the semiconductor integrated circuit 100 contacting with multiple probes 2 during the testing.

Figure 2:
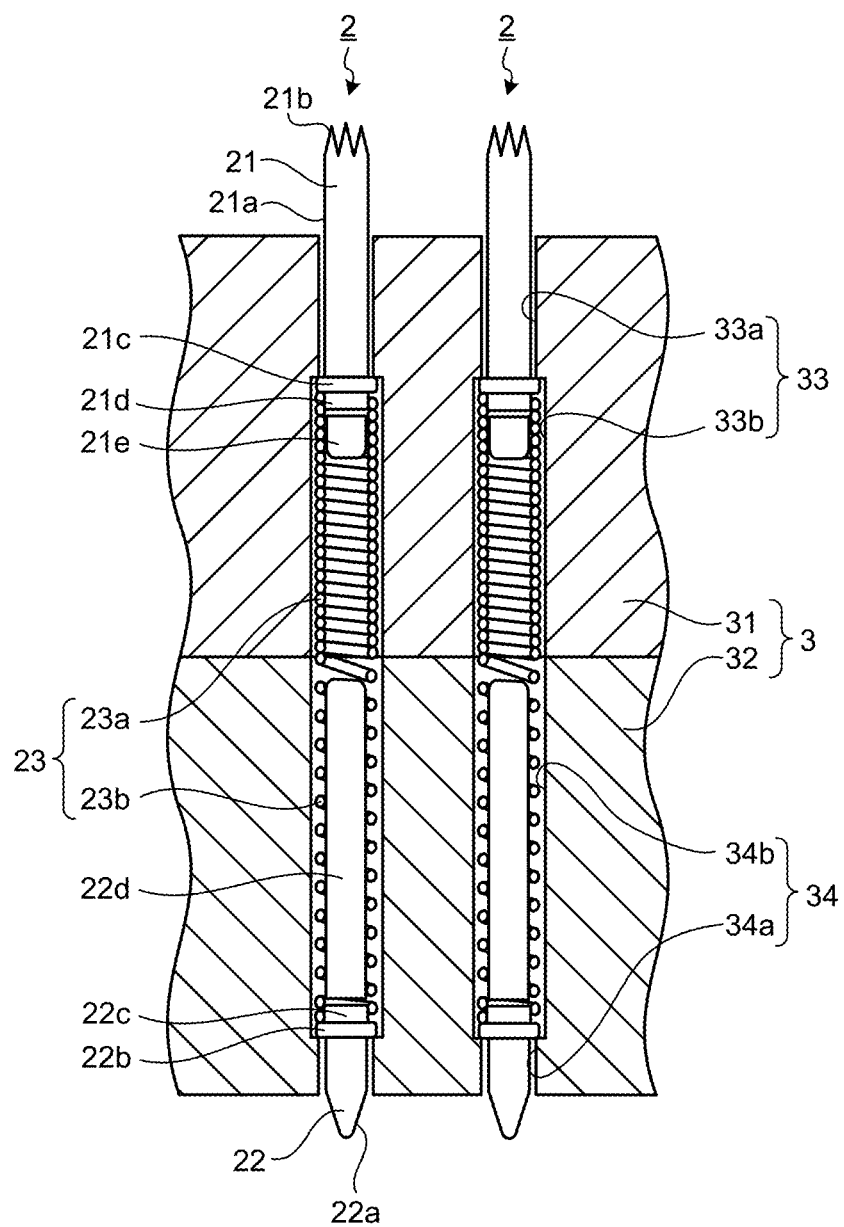
FIG. 2 is a local sectional view illustrating a configuration of the main section of a socket according to one use mode of an alloy material in an embodiment of the present invention.

FIG. 2 is a local sectional view illustrating a configuration of the main section of a socket (contact probe) according to one use mode of an alloy material of the present embodiment, and illustrating the detailed configuration of the probes 2 to be housed in a probe holder 3. The probes 2 illustrated in FIG. 2 are provided with a first plunger 21 that contacts with an connection electrode of the semiconductor integrated circuit 100; a second plunger 22 that contacts with an electrode of a circuit board 200 provided with a test circuit; and a coil spring 23 that is arranged between the first plunger 21 and the second plunger 22, and elastically connects two of the first plunger 21 and the second plunger 22 with each other, when the testing of the semiconductor integrated circuit 100 is performed. The first plunger 21 and the second plunger 22, and the coil spring 23, which configure probe 2, have the same axis. The probe 2 reduces the impact on a connection electrode of semiconductor integrated circuit 100 by the expansion and contraction of the coil spring 23 in the axial direction, and further applies a load to the semiconductor integrated circuit 100 and the circuit board 200, when contacting with the semiconductor integrated circuit 100.

The first plunger 21 has an end portion 21*a* that has a pawl portion 21*b* with a tapered tip shape in multiple numbers; a flange portion 21*c* that extends from the proximal end side of the end portion 21*a* and has larger diameter than that of the end portion 21*a*; a boss part 21*d* that extends from the end different from the side connected to the end portion 21*a* of the flange portion 21*c* and has smaller diameter than that of the flange portion 21*c*; and a proximal end portion 21*e* that extends from the end different from the side connected to the flange portion 21*c* of the boss part 21*d* and has nearly the same diameter as that of the boss part 21*d*, on the same axis. Further, the proximal end portion 21*e* has a tip with an R-chamfered shape.

The second plunger 22 has an end portion 22*a* that has a tapered tip shape; a flange portion 22*b* that extends from the proximal end side of the end portion 22*a* and has larger diameter than that of the end portion 22*a*; a boss part 22*c* that extends from the end different from the side connected to the end portion 22*a* of the flange portion 22*b* and has nearly the same diameter as that of the boss part 21*d*; and a proximal end portion 22*d* that extends from the end different from the side connected to the flange portion 22*b* of the boss part 22*c* and has nearly the same diameter as that of the boss parts 21*d* and 22*c*, on the same axis. The second plunger 22 can move in the axial direction by the expansion and contraction action of the coil spring 23, is energized in the direction of the circuit board 200 by the elastic force of the coil spring 23, and contacts with an electrode of the circuit board 200.

The coil spring 23 has a tightly wound coil part 23*a* that is wound with nearly the same inner diameter as the diameter of the boss part 21*d* on the side of the first plunger 21, and on the other hand, has a roughly wound coil part 23*b* that is wound in a predetermined pitch with an inner diameter of the diameter of the proximal end portion 22*d* or more on the side of the second plunger 22. The end of the tightly wound coil part 23*a* is, for example, if having nearly the same inner diameter as that of the boss part 21*d*, pressed by the boss part 21*d* and abutted on the flange portion 21*c*. On the other hand, the end of the roughly wound coil part 23*b* is pressed by the boss part 22*c* and abutted on the flange portion 22*b*. In addition, in the coil spring 23, the tightly wound coil part 23*a* and the roughly wound coil part 23*b* are preferably wound with the same inner diameter as each other. At this time, the first plunger 21, the second plunger 22, and the coil spring 23 may be joined by soldering.

At least one of the first plunger 21, the second plunger 22, and the coil spring 23 is formed using the alloy material described above, and all of the members are preferably formed using the alloy material. Further, the coil spring 23 is designed to have a diameter of wire, and a diameter formed by winding the wire so as to obtain the spring characteristic in which when the contraction amount of the roughly wound coil part 23*b* when the predetermined load is applied is, for example, larger than the shortest distance between the proximal end portion 22*d* and the tightly wound coil part 23*a* in the state that the probe 2 is housed in the probe holder 3 (see FIG. 1) when the initial load is applied. By using the coil spring 23 having the spring characteristic, when the predetermined load is applied to the probe 2, a proximal end portion 22*d* is in sliding contact with a tightly wound coil part 23*a*, and the electrical continuity can be provided between the proximal end portion 22*d* and the tightly wound coil part 23*a*.

A probe holder 3 is formed by using an insulating material such as a resin, machinable ceramics, and silicon, and made by the lamination of the first member 31 positioned in the upper side and the second member 32 positioned in the lower side in FIG. 2. In the first member 31 and second member 32, holder holes 33 and 34 are formed in the same number as each other for housing the multiple probes 2, and the holder holes 33 and 34 for housing the probe 2 are formed so as to match the axes with each other. The formation position of the holder holes 33 and 34 is determined according to the wiring pattern of semiconductor integrated circuit 100.

Both of the holder holes 33 and 34 are formed in a stepped hole shape having different diameters along the passing direction. That is, the holder hole 33 consists of a small diameter part 33*a* having opening in the upper end face of the probe holder 3, and a large diameter part 33*b* having a larger diameter than that of the small diameter part 33*a*. The small diameter part 33*a* has a slightly larger diameter as compared with the diameter of the end portion 21*a*. Further, the large diameter part 33*b* has a slightly larger diameter as compared with the diameter of the flange portion 21*c* and/or the diameter of the coil spring 23.

On the other hand, the holder hole 34 consists of a small diameter part 34*a* having opening in the lower end face of the probe holder 3, and a large diameter part 34*b* having a larger diameter than that of the small diameter part 34*a*. The small diameter part 34*a* has a slightly larger diameter as compared with that of the end portion 22*a*. Further, the large diameter part 34*b* has a slightly larger diameter as compared with the diameter of the flange portion 22*b* and/or the diameter of the coil spring 23. The shapes of these holder holes 33 and 34 are determined according to the configuration of the probe 2 to be housed.

The flange portion 21*c* of the first plunger 21 has a function of preventing the probe 2 from falling from the probe holder 3 by abutting on the boundary wall surface between the small diameter part 33*a* and the large diameter part 33*b* of the holder hole 33. The flange portion 22*b* of the second plunger 22 has a function of preventing the probe 2 from falling from the probe holder 3 by abutting on the boundary wall surface between the small diameter part 34a and the large diameter part 34b of the holder hole 34. Further, each boundary wall surface of the holder holes 33 and 34 may be a stepped shape corresponding to the diameters of the flange portions 21c, 22b, and the coil spring 23, respectively.

Figure 3:
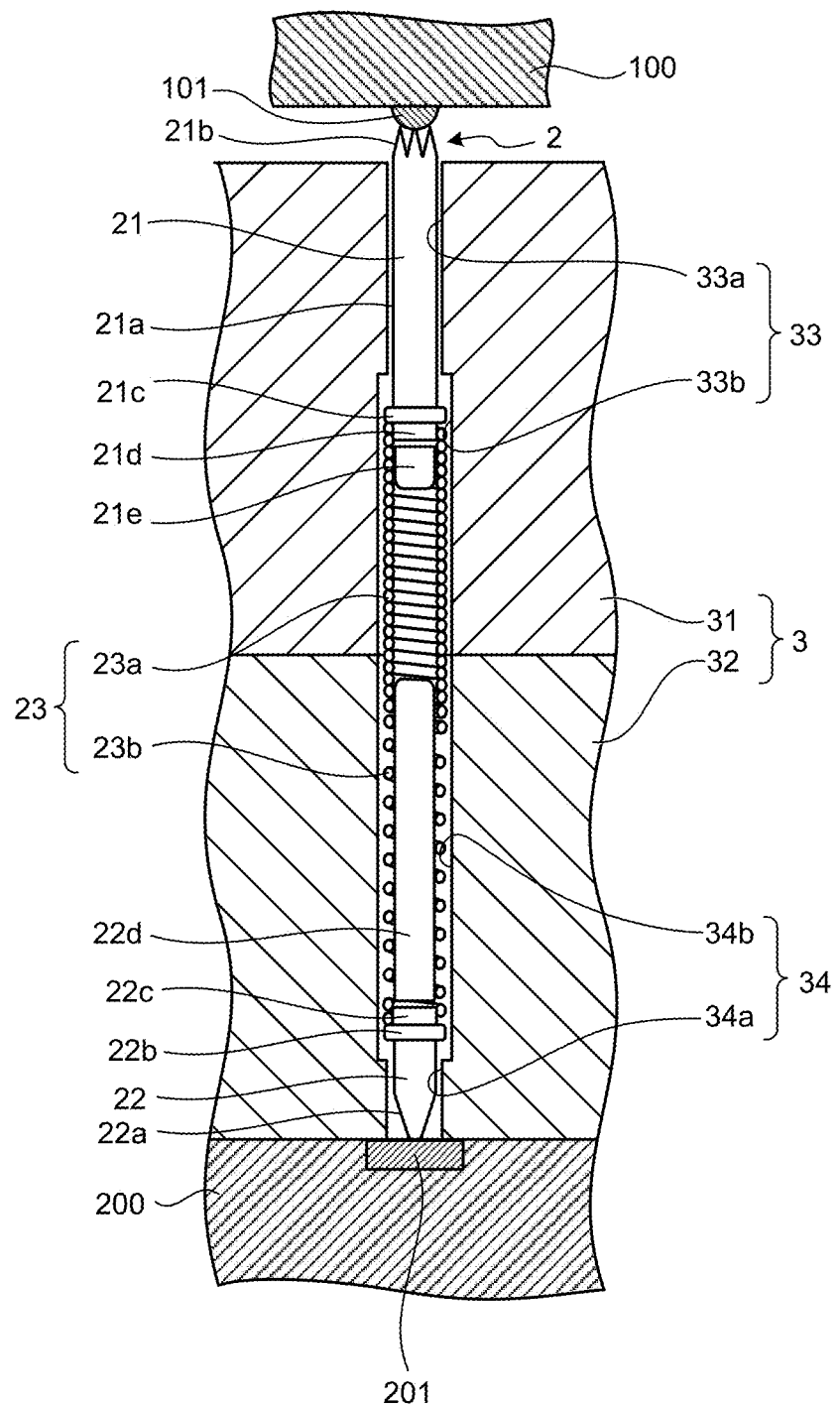
FIG. 3 is a local sectional view illustrating a configuration of the main section of a socket during testing of a socket according to one use mode of an alloy material in an embodiment of the present invention.

FIG. 3 is a local sectional view illustrating a configuration of the main section of a socket during the testing of a semiconductor integrated circuit in a socket (contact probe) according to one use mode of an alloy material of the present embodiment, and illustrating the state during the testing of a semiconductor integrated circuit 100 by using a probe holder 3. During the testing of the semiconductor integrated circuit 100, the coil spring 23 becomes in a compressed state along the longitudinal direction by the contact load from the semiconductor integrated circuit 100. When the coil spring 23 is compressed, as illustrated in FIG. 3, the proximal end portion 22d of the second plunger 22 enters the tightly wound coil part 23a, and is in sliding contact with the inner peripheral side of the tightly wound coil part 23a. Herein, the axis of the second plunger 22 does not largely deviate, therefore, the sliding contact between the proximal end portion 22d and the tightly wound coil part 23a becomes stable, and further the tightly wound coil part 23a slightly meanders, as a result, the contact resistance of the proximal end portion 22d and the coil spring 23 becomes stable, and the reliable continuity can be obtained.

During the testing, the signals for testing supplied from the circuit board 200 to the semiconductor integrated circuit 100 reach a connection electrode 101 of the semiconductor integrated circuit 100 via the probe 2 from an electrode 201 of the circuit board 200, respectively. Specifically, in the probe 2, the signal reaches the connection electrode 101 of the semiconductor integrated circuit 100 via the second plunger 22, the tightly wound coil part 23a, and the first plunger 21. As described above, in the probe 2, the first plunger 21 is conducted with the second plunger 22 via the tightly wound coil part 23a, therefore, the conductive path of electric signals can be minimized. Therefore, the signals are prevented from flowing to the roughly wound coil part 23b during the testing, and the reduction and stabilization of the inductance can be realized.

Further, the tip of the pawl portion 21b is formed in a tapered shape, therefore, even in a case where an oxide film is formed on the surface of the connection electrode 101, the tip of the pawl portion 21b can directly be contacted with the connection electrode 101 by breaking through the oxide film.

Figure 4:
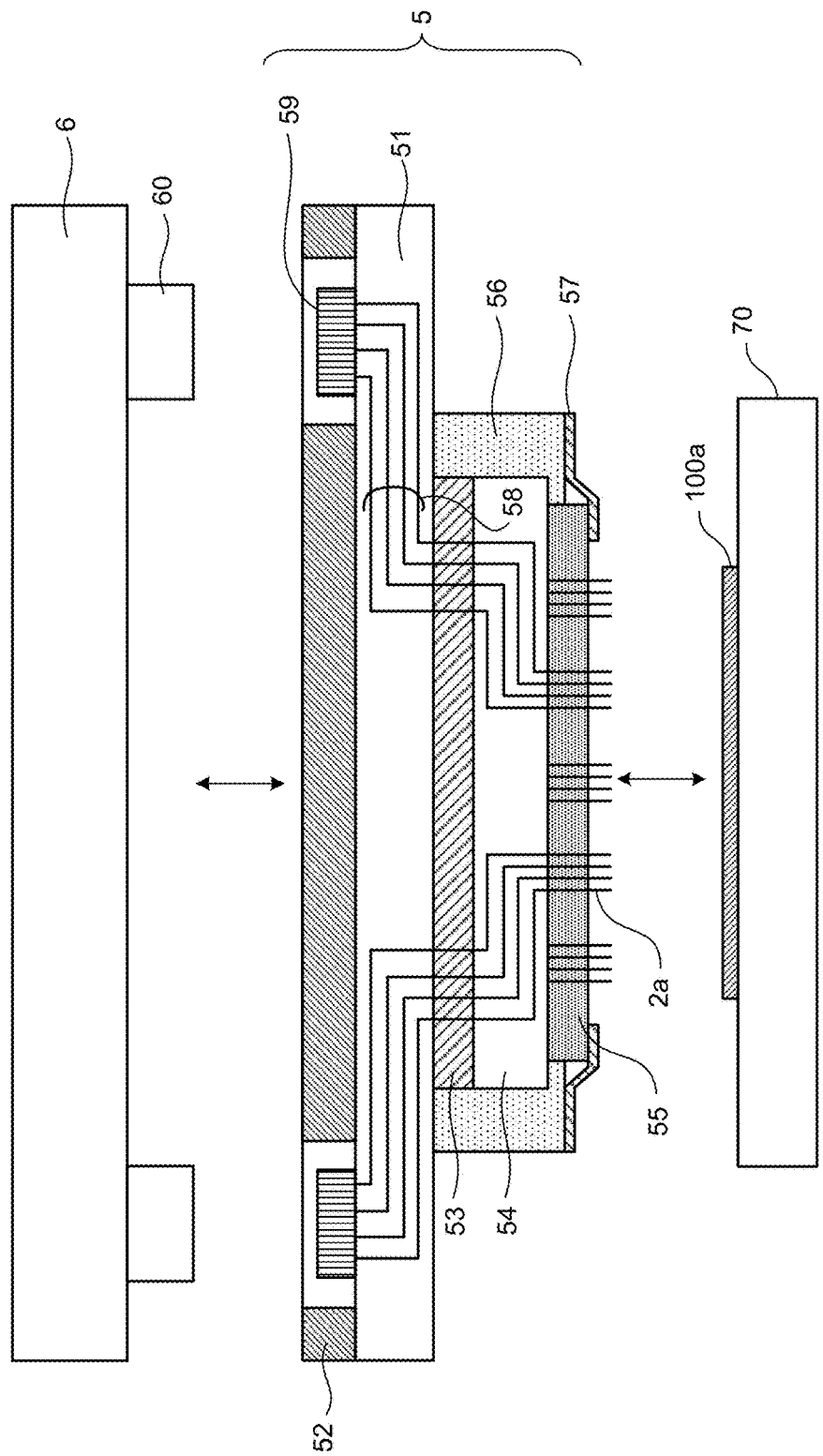
FIG. 4 is a local sectional view illustrating a configuration of a probe card according to another use mode of an alloy material in an embodiment of the present invention.

FIG. 4 is a local sectional view illustrating a configuration of a probe card 5 according to another use mode of an alloy material in an embodiment of the present invention. The probe card 5 performs an electric characteristic testing by contacting with the probe having conductivity with the state of the semiconductor wafer before dicing, and detects the defective products (wafer level test).

Probe card 5 is formed in a thin disk shape, and provided with a substrate 51 that achieves the electrical connection with a testing apparatus (not illustrated); a reinforcing member 52 that is attached on one surface of the substrate 51 and reinforces the substrate 51; an interposer 53 that relays the wiring from the substrate 51; a space transformer 54 that converts the space of the wiring relaid by the interposer 53; and a probe head 55 that is formed in a disk shape having a diameter smaller than that of the substrate 51 and laminated on the space transformer 54, and houses and holds multiple probes 2a corresponding to the wiring pattern of the test target. Further, the probe card 5 is fixed on the substrate 51, and provided with a holding member 56 that collectively holds the interposer 53 and the space transformer 54 in a laminated state, and a leaf spring 57 that is fixed on the holding member 56 and fastens the ends of the probe head 55.

Further, one end of a wiring 58 formed on the substrate 51 is connected with the multiple male connectors 59 arranged on the surface on the side attached with reinforcing member 52, which is the surface of the substrate 51, in order to connect with a testing apparatus, on the other hand, the other end of the wiring 58 is connected with the probe 2a that is housed and held with the probe head 55 via an electrode pad 541 (see FIG. 5) formed in the lower end of the space transformer 54. In addition, in FIG. 4, in order to simplify the description, part of the wiring 58 is only illustrated.

Each male connector 59 is arranged radially with respect to the center of the substrate 51, makes a pair with female connectors 60 that are provided at a position facing in the connector pedestal 6 of a testing apparatus, respectively, and establishes the electrical connection of the probe 2a and the testing apparatus by contacting the terminals with each other.

Figure 5:
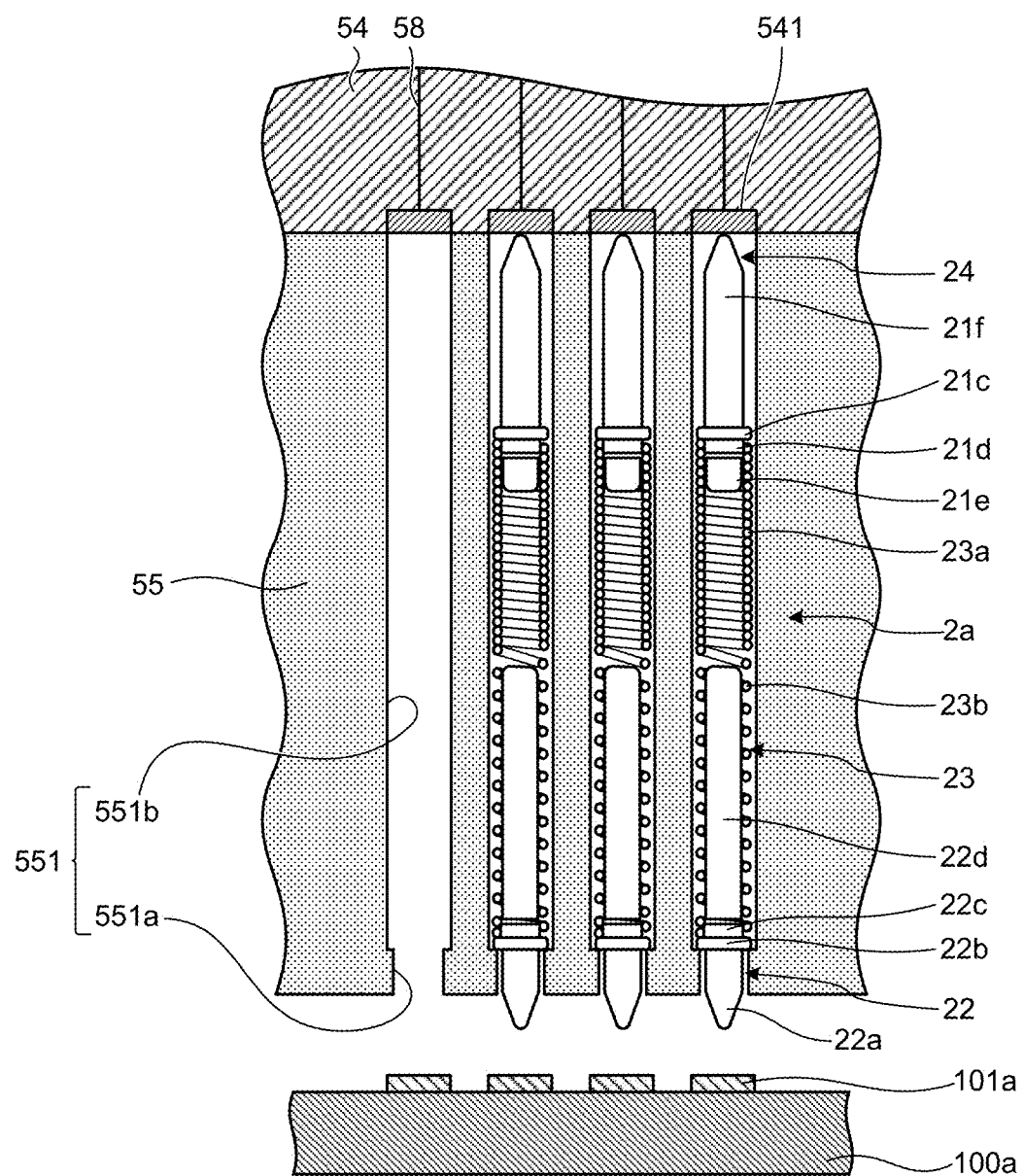
FIG. 5 is a local sectional view illustrating a configuration of the main section of a probe card according to another use mode of an alloy material in an embodiment of the present invention.

FIG. 5 is a local sectional view illustrating a configuration of the main section of a probe card 5. The probe 2a illustrated in FIG. 5 is arranged so as to protrude one tip corresponding to the arrangement pattern of a connection electrode 101a of a semiconductor wafer 100a placed on a wafer chuck 70 (see FIG. 4), the tip (bottom side) of each probe 2a is contacted from the direction perpendicular to the surface of multiple electrodes for connection 101a of the semiconductor wafer 100a.

The probe 2a is provided with a first plunger 24, the tip of which contacts with an electrode pad 541 (object to be contacted) of space transformer 54; a second plunger 22 that contacts with a connection electrode 101a (object to be contacted) of the semiconductor wafer 100a that is a test target; and a coil spring 23 that is arranged between the plungers 24 and 22, and elastically connects the first plunger 24 and the second plunger 22. The first plunger 24, the second plunger 22, and the coil spring 23, which are connected to each other, have the same axis. Further, the second plunger 22 and the coil spring 23 have the configuration described above. In addition, to the same constituent elements as those of the configuration explained in FIG. 1 and the like, the same signs are denoted.

The first plunger 24 has an end portion 21f that has a tapered tip shape; a flange portion 21c that extends from the proximal end side of the end portion 21f and has larger diameter than the diameter of the end portion 21f; and the boss part 21d and proximal end portion 21e described above, on the same axis.

The probe head 55 is formed by using, for example, an insulating material such as ceramics. In the probe head 55, holder holes 551 that house the probes 2a separately are provided passing through in the thickness direction (vertical direction in FIG. 5) of the probe head 55 depending on the array of a connection electrode 101a of the semiconductor wafer 100a. The holder hole 551 is provided with a small diameter part 551a that is formed over the length at least shorter than the length of the end portion 22a in the longitudinal direction, and a large diameter part 551b that has the same central axis as that of the small diameter part and the larger diameter than the diameter of the small diameter part 551a, from the end face on the side of the semiconductor wafer 100a. The inner diameter of the small diameter hole 551*a* is slightly larger than the outer diameter of the end portion 22*a*, and slightly smaller than the outer diameter of the flange portion 22*b*. Therefore, the holder hole 551 prevents the second plunger 22 from falling.

The number and arrangement pattern of the probe 2*a* housed in the probe head 55 is determined depending on the number of the semiconductor chips formed on the semiconductor wafer 100*a* and the arrangement pattern of the connection electrode 101*a*. For example, in a case where the semiconductor wafer 100*a* having a diameter of eight inches (around 200 mm) is used as a test target, tens to thousands of probes 2*a* are required. Further, in a case where the semiconductor wafer 100*a* having a diameter of two inches (around 300 mm) is used as a test target, hundreds to thousands of probes 2*a* are required.

During the test of the semiconductor wafer 100*a*, as illustrated in FIG. 3, the coil spring 23 becomes in a compressed state along the longitudinal direction by the contact load from the semiconductor wafer 100*a*. When the coil spring 23 is compressed, the proximal end portion 22*d* of the second plunger 22 enters the tightly wound coil part 23*a* and is in sliding contact with the inner peripheral side of the tightly wound coil part 23*a*. Herein, the axis of the second plunger 22 does not largely deviate, therefore, the sliding contact between the proximal end portion 22*d* and the tightly wound coil part 23*a* becomes stable, and further the tightly wound coil part 23*a* slightly meanders, as a result, the contact resistance of the proximal end portion 22*d* and the coil spring 23 becomes stable, and the reliable continuity can be obtained.

Further, the configuration of probes 2, and 2*a* explained above is only one example, the alloy material described above may be applied to various kinds of probes that have conventionally been known. For example, not only the one configured with the above-described plunger and coil spring, but also a pogo pin, a wire probe that obtains a load by bending a wire in an arcuate shape, or a connection terminal (connector) that connects electrical contacts with each other may be used.

Herein, the connection terminal connects electrical contacts with each other, for example, as the probes 2, and 2*a* described above, is provided with two conductive terminals that contact with each of the electrical contacts, respectively, and with an elastic member (or holding member) that holds slidably each terminal. In such a connection terminal, at least the terminal consists of the alloy material described above.

EXAMPLES

Hereinafter, Examples and Comparative Examples of the alloy material in the present invention will be explained in detail. Firstly, the production and measurement content of the alloy material according to the present Examples will be explained.

Each alloy material according to Examples or Comparative Examples was blended in predetermined composition, subjected to high frequency melting, and prepared as an ingot of round bar (ϕ5 mm, and the length 1000 mm). The test piece for hardness used for a hardness test was prepared as follows. The ingot described above was cut off to obtain two ingots cut into ϕ5 mm and the length 50 mm, and then the two ingots were subjected to a solution treatment by being heated at 850° C. for one hour, and cooled. After that, one cut ingot that had been cut out was cut into ϕ5 mm and the length 10 mm to prepare test pieces for hardness. By using a Vickers hardness testing machine, the Vickers hardness of the test piece for hardness (solution treated material) after the solution treatment was measured. Further, the other cut ingot that had been solution treated was heated at 400° C. for one hour (aging treatment), and then was cut into ϕ5 mm and the length 10 mm to prepare test pieces for hardness (aged material), and the Vickers hardness after the aging treatment was measured.

The test piece for electric conductivity was prepared as follows. The ingot prepared earlier was cut into ϕ5 mm and the length 200 mm, and subjected to a solution treatment by being heated at 850° C. for one hour, and cooled. After that, the solution treated material that had been subjected to solution treatment was rolled up to ϕ2.0 mm by a wire drawing machine, and to which a working rate of 84% was added. After that, the solution treated material that had been rolled was heated at 400° C. for one hour (aging treatment), cut into ϕ2 mm and the length 300 mm, and prepared as a test piece for electric conductivity. By using an electric resistance measuring machine, a resistance of the test piece for electric conductivity was measured, and the electric conductivity was determined.

As to the workability, the propriety of the workability and the surface crack when a working rate of 84% was added (rolling) were observed in the test piece for electric conductivity with an optical microscope. The evaluation of the workability was performed by describing O when the working could be performed without breaking with no cracks, Δ when the working could be performed without breaking with cracks, and x when the working could not be performed with breaking.

Next, the atomic ratio of each metal of the alloy material according to the present Examples will be explained. Table 1 shows the atomic ratio (composition) and measurement results of each of the alloy materials according to Examples 1 to 32. Table 2 shows the atomic ratio and measurement results of each of the alloy materials according to Comparative Examples 1 to 17. In Examples 1 to 13, the composition is that 3.5 at % of Mn was added based on the ternary alloy of Ag—Pd—Cu consisting of 17 at % to 25 at % of Ag, 30 at % to 45 at % of Pd, and 30 at % to 53 at % of Cu in the atomic ratio; or the composition is that 0.5 at % to 3.5 at % of Mn was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In addition, in Example 2, the final atomic ratios of Ag and Pd were lower than 17 at % by the addition of Mn, Ir, and Ru. Further, in Example 11, the final atomic ratio of Cu was lower than 30 at % by the addition of Mn, and Ir.

TABLE 1

| No. | Ag [at %] | Pd [at %] | Cu [at %] | Mn [at %] | Sn [at %] | Si [at %] | Sb [at %] | Ti [at %] | Mg [at %] | Ir [at %] |
|---|---|---|---|---|---|---|---|---|---|---|
| Example 1 | 20.00 | 36.50 | 40.00 | 3.50 | — | — | — | — | — | — |
| Example 2 | 16.50 | 29.10 | 51.35 | 3.00 | — | — | — | — | — | 0.02 |

TABLE 1-continued

| No. | | | | | | | | | | |
|---|---|---|---|---|---|---|---|---|---|---|
| Example 3 | 17.50 | 33.90 | 45.55 | 3.00 | — | — | — | — | — | 0.03 |
| Example 4 | 17.50 | 39.00 | 40.95 | 2.50 | — | — | — | — | — | — |
| Example 5 | 20.00 | 38.50 | 41.45 | 0.50 | — | — | — | — | — | 0.05 |
| Example 6 | 21.30 | 34.00 | 41.69 | 3.00 | — | — | — | — | — | 0.01 |
| Example 7 | 21.20 | 38.60 | 36.65 | 3.50 | — | — | — | — | — | 0.05 |
| Example 8 | 19.30 | 36.65 | 40.52 | 3.50 | — | — | — | — | — | 0.03 |
| Example 9 | 19.30 | 38.60 | 38.59 | 3.50 | — | — | — | — | — | — |
| Example 10 | 21.80 | 37.10 | 40.06 | 1.00 | — | — | — | — | — | 0.04 |
| Example 11 | 24.10 | 43.40 | 28.96 | 3.50 | — | — | — | — | — | 0.04 |
| Example 12 | 24.40 | 29.20 | 43.87 | 2.50 | — | — | — | — | — | 0.03 |
| Example 13 | 24.35 | 33.05 | 41.55 | 1.00 | — | — | — | — | — | 0.05 |
| Example 14 | 16.60 | 44.10 | 37.25 | — | 2.00 | — | — | — | — | — |
| Example 15 | 19.60 | 37.25 | 41.12 | — | 2.00 | — | — | — | — | 0.03 |
| Example 16 | 21.80 | 39.60 | 37.55 | — | 1.00 | — | — | — | — | 0.02 |
| Example 17 | 20.20 | 38.50 | 40.75 | — | — | 0.50 | — | — | — | 0.03 |
| Example 18 | 23.80 | 32.80 | 41.35 | — | — | 2.00 | — | — | — | 0.05 |
| Example 19 | 20.10 | 35.20 | 44.15 | — | — | — | 0.50 | — | — | — |
| Example 20 | 21.70 | 35.30 | 39.97 | — | — | — | 3.00 | — | — | 0.03 |
| Example 21 | 21.10 | 36.20 | 42.15 | — | — | — | — | 0.50 | — | 0.05 |
| Example 22 | 22.20 | 36.40 | 39.36 | — | — | — | — | 2.00 | — | — |
| Example 23 | 21.10 | 37.70 | 40.65 | — | — | — | — | — | 0.50 | 0.03 |
| Example 24 | 19.80 | 37.10 | 39.58 | — | — | — | — | — | 3.50 | 0.02 |
| Example 25 | 20.00 | 35.50 | 39.97 | 3.50 | 1.00 | — | — | — | — | 0.03 |
| Example 26 | 20.00 | 37.00 | 39.97 | 2.00 | — | 1.00 | — | — | — | — |
| Example 27 | 20.00 | 37.00 | 39.95 | 1.00 | 1.00 | 1.00 | — | — | — | 0.03 |
| Example 28 | 19.40 | 36.40 | 40.65 | 2.50 | — | — | 1.00 | — | — | 0.05 |
| Example 29 | 19.50 | 38.00 | 40.47 | — | 1.50 | — | — | 0.50 | — | 0.03 |
| Example 30 | 20.30 | 35.80 | 41.37 | — | — | 1.00 | — | — | 1.50 | — |
| Example 31 | 21.10 | 35.50 | 39.85 | — | — | — | 2.00 | 1.50 | — | — |
| Example 32 | 21.40 | 36.30 | 39.25 | — | — | — | 1.00 | 1.00 | 1.00 | 0.05 |
| Example 7-1 | 21.20 | 38.60 | 36.65 | 3.50 | — | — | — | — | — | 0.05 |
| Example 7-2 | 21.20 | 38.60 | 36.65 | 3.50 | — | — | — | — | — | 0.05 |
| Example 7-3 | 21.20 | 38.60 | 36.65 | 3.50 | — | — | — | — | — | 0.05 |

| No. | Ru [at %] | In [at %] | Solution treated material Hardness [HV] | Aged material Hardness [HV] | Electric conductivity [(μΩ · m)−1] | Workability | Remarks |
|---|---|---|---|---|---|---|---|
| Example 1 | — | — | 206 | 543 | 8.11 | ○ | |
| Example 2 | 0.03 | — | 206 | 507 | 8.72 | ○ | |
| Example 3 | 0.02 | — | 214 | 521 | 8.32 | ○ | |
| Example 4 | 0.05 | — | 205 | 522 | 8.68 | ○ | |
| Example 5 | — | — | 211 | 517 | 8.89 | ○ | |
| Example 6 | — | — | 214 | 524 | 8.4 | ○ | |
| Example 7 | — | — | 207 | 536 | 8.38 | ○ | |
| Example 8 | — | — | 211 | 554 | 8.3 | ○ | |
| Example 9 | 0.01 | — | 205 | 523 | 8.25 | ○ | |
| Example 10 | — | — | 213 | 529 | 8.87 | ○ | |
| Example 11 | — | — | 210 | 492 | 8.01 | ○ | |
| Example 12 | — | — | 203 | 487 | 8.85 | ○ | |
| Example 13 | — | — | 207 | 508 | 8.91 | ○ | |
| Example 14 | 0.05 | — | 225 | 506 | 8.13 | ○ | |
| Example 15 | — | — | 237 | 553 | 8.37 | ○ | |
| Example 16 | 0.03 | — | 220 | 526 | 8.05 | ○ | |
| Example 17 | 0.02 | — | 216 | 523 | 8.31 | ○ | |
| Example 18 | — | — | 252 | 494 | 8.02 | ○ | |
| Example 19 | 0.05 | — | 212 | 512 | 8.53 | ○ | |
| Example 20 | — | — | 234 | 524 | 8.21 | ○ | |
| Example 21 | — | — | 243 | 515 | 8.55 | ○ | |
| Example 22 | 0.04 | — | 259 | 526 | 8.24 | ○ | |
| Example 23 | 0.02 | — | 214 | 511 | 8.46 | ○ | |
| Example 24 | — | — | 222 | 523 | 8.65 | ○ | |
| Example 25 | — | — | 226 | 530 | 8.13 | ○ | |
| Example 26 | 0.03 | — | 234 | 528 | 8.11 | ○ | |
| Example 27 | 0.02 | — | 229 | 525 | 8.21 | ○ | |
| Example 28 | — | — | 234 | 525 | 8.17 | ○ | |
| Example 29 | — | — | 241 | 529 | 8.12 | ○ | |
| Example 30 | 0.03 | — | 217 | 528 | 8.27 | ○ | |
| Example 31 | 0.05 | — | 247 | 525 | 8.31 | ○ | |
| Example 32 | — | — | 235 | 523 | 8.34 | ○ | |
| Example 7-1 | — | — | 207 | 540 | 8.36 | ○ | Aging treatment temperature: 300° C. |
| Example 7-2 | — | — | 207 | 541 | 8.36 | ○ | Aging treatment temperature: 350° C. |

TABLE 1-continued

| | | | | | | | |
|---|---|---|---|---|---|---|---|
| Example 7-3 | — | — | 207 | 481 | 8.42 | ○ | Aging treatment temperature: 450° C. |

TABLE 2

| No. | Ag [at %] | Pd [at %] | Cu [at %] | Mn [at %] | Sn [at %] | Si [at %] | Sb [at %] | Ti [at %] | Mg [at %] | Ir [at %] |
|---|---|---|---|---|---|---|---|---|---|---|
| Comparative Example 1 | 18.00 | 35.00 | 47.00 | — | — | — | — | — | — | — |
| Comparative Example 2 | 18.00 | 40.00 | 42.00 | — | — | — | — | — | — | — |
| Comparative Example 3 | 22.00 | 35.00 | 43.00 | — | — | — | — | — | — | — |
| Comparative Example 4 | 22.00 | 40.00 | 38.00 | — | — | — | — | — | — | — |
| Comparative Example 5 | 24.00 | 37.00 | 39.00 | — | — | — | — | — | — | — |
| Comparative Example 6 | 15.00 | 38.00 | 47.00 | — | — | — | — | — | — | — |
| Comparative Example 7 | 14.40 | 33.80 | 48.30 | 3.50 | — | — | — | — | — | — |
| Comparative Example 8 | 14.70 | 34.30 | 49.00 | — | 2.00 | — | — | — | — | — |
| Comparative Example 9 | 20.00 | 36.00 | 40.00 | 4.00 | — | — | — | — | — | — |
| Comparative Example 10 | 17.50 | 38.80 | 40.66 | — | 3.00 | — | — | — | — | 0.04 |
| Comparative Example 11 | 21.30 | 36.30 | 39.35 | — | — | 3.00 | — | — | — | 0.05 |
| Comparative Example 12 | 17.20 | 33.40 | 45.37 | — | — | — | 4.00 | — | — | — |
| Comparative Example 13 | 21.40 | 33.80 | 41.75 | — | — | — | — | 3.00 | — | — |
| Comparative Example 14 | 21.20 | 38.40 | 36.35 | — | — | — | — | — | 4.00 | 0.03 |
| Comparative Example 15 | 20.00 | 35.50 | 40.00 | 3.50 | 2.00 | — | — | — | — | — |
| Comparative Example 16 | 24.35 | 33.05 | 41.55 | — | — | — | — | — | — | 0.05 |
| Comparative Example 17 | 20.00 | 35.50 | 39.95 | 3.50 | — | — | — | — | — | 0.05 |
| Comparative Example 18-1 | 21.20 | 38.60 | 36.65 | 3.50 | — | — | — | — | — | 0.05 |
| Comparative Example 18-2 | 21.20 | 38.60 | 36.65 | 3.50 | — | — | — | — | — | 0.05 |

| No. | Ru [at %] | In [at %] | Solution treated material Hardness [HV] | Aged material Hardness [HV] | Electric conductivity [(μΩ · m)−1] | Workability | Remarks |
|---|---|---|---|---|---|---|---|
| Comparative Example 1 | — | — | 196 | 451 | 9.32 | ○ | |
| Comparative Example 2 | — | — | 192 | 448 | 9.81 | ○ | |
| Comparative Example 3 | — | — | 206 | 457 | 9.86 | ○ | |
| Comparative Example 4 | — | — | 196 | 447 | 9.54 | ○ | |
| Comparative Example 5 | — | — | 209 | 443 | 9.68 | ○ | |
| Comparative Example 6 | — | — | 193 | 405 | 10.82 | ○ | |
| Comparative Example 7 | — | — | 186 | 347 | 8.19 | ○ | |
| Comparative Example 8 | — | — | 221 | 361 | 8.17 | ○ | |
| Comparative Example 9 | — | — | 166 | 489 | — | X | |
| Comparative Example 10 | — | — | 270 | 555 | — | X | |
| Comparative Example 11 | — | — | 289 | 528 | — | X | |

TABLE 2-continued

| | | | | | | |
|---|---|---|---|---|---|---|
| Comparative Example 12 | 0.03 | — | 231 | 511 | — | X |
| Comparative Example 13 | 0.05 | — | 268 | 497 | — | X |
| Comparative Example 14 | 0.02 | — | 224 | 493 | — | X |
| Comparative Example 15 | — | — | 226 | 536 | — | X |
| Comparative Example 16 | — | 1.00 | 203 | 470 | 8.83 | ○ |
| Comparative Example 17 | — | 1.00 | 220 | 525 | 8.24 | Δ |
| Comparative Example 18-1 | — | — | 207 | 380 | 11.51 | ○ Aging treatment temperature: 275° C. |
| Comparative Example 18-2 | — | — | 207 | 401 | 10.90 | ○ Aging treatment temperature: 475° C. |

In Examples 14 to 16, the composition is that 1 at % to 2 at % of Sn was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. Further, in Example 14, the final atomic ratio of Ag was lower than 17 at % by the addition of Sn, and Ru.

In Examples 17 and 18, the composition is that 0.5 at % to 2 at % of Si was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio.

In Examples 19 and 20, the composition is that 0.5 at % to 3 at % of Sb was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio.

In Examples 21 and 22, the composition is that 0.5 at % to 2 at % of Ti was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio.

In Examples 23 and 24, the composition is that 0.5 at % to 3.5 at % of Mg was added, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio.

In Examples 25 to 32, the composition is that the 0.5 at % to 3.5 at % of Mn, 1 at % to 2 at % of Sn, 0.5 at % to 2 at % of Si, 0.5 at % to 3 at % of Sb, 0.5 at % to 2 at % of Ti, and 0.5 at % to 3.5 at % of Mg in combination were added in a range not exceeding 4.5 at %, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio.

In Comparative Examples 1 to 5, the alloy is a ternary alloy of Ag—Pd—Cu consisting of 17 at % to 25 at % of Ag, 30 at % to 45 at % of Pd, and 30 at % to 53 at % of Cu in the atomic ratio. In Comparative Example 6, the composition is outside the composition range described above.

In Comparative Examples 7 and 8, the composition has a low amount of Ag outside the range of 17 at % to 25 at % of Ag, 30 at % to 45 at % of Pd, and 30 at % to 53 at % of Cu in the atomic ratio. Further, in Comparative Example 7, the composition is that 3.5 at % of Mn was added, and in Comparative Example 8, the composition is that 2 at % of Sn was added, based on the ternary alloy of Ag—Pd—Cu.

In Comparative Example 9, the composition is that 4 at % (>3.5 at %) of Mn was added to a ternary alloy of Ag—Pd—Cu consisting of 17 at % to 25 at % (the final atomic ratio 20.00 at %) of Ag, 30 at % to 45 at % (36.00 at %) of Pd, and 30 at % to 53 at % (40.00 at %) of Cu in the atomic ratio.

In Comparative Example 10, the composition is that 3 at % (>2 at %) of Sn and 0.04 at % of Ir were added to a ternary alloy of Ag—Pd—Cu consisting of 17 at % to 25 at % (17.50 at %) of Ag, 30 at % to 45 at % (38.80 at %) of Pd, and 30 at % to 53 at % (40.66 at %) of Cu in the atomic ratio.

In Comparative Example 11, the composition is that 3 at % (>2 at %) of Si and 0.05 at % of Ir were added to a ternary alloy of Ag—Pd—Cu consisting of 17 at % to 25 at % (21.30 at %) of Ag, 30 at % to 45 at % (36.30 at %) of Pd, and 30 at % to 53 at % (39.35 at %) of Cu in the atomic ratio.

In Comparative Example 12, the composition is that 4 at % (>3 at %) of Sb and 0.03 at % of Ru were added to a ternary alloy of Ag—Pd—Cu consisting of 17 at % to 25 at % (17.20 at %) of Ag, 30 at % to 45 at % (33.40 at %) of Pd, and 30 at % to 53 at % (45.37 at %) of Cu in the atomic ratio.

In Comparative Example 13, the composition is that 3 at % (>2 at %) of Ti and 0.05 at % of Ru were added to a ternary alloy of Ag—Pd—Cu consisting of 17 at % to 25 at % (21.40 at %) of Ag, 30 at % to 45 at % (33.80 at %) of Pd, and 30 at % to 53 at % (41.75 at %) of Cu in the atomic ratio.

In Comparative Example 14, the composition is that 4 at % (>3.5 at %) of Mg was added, and the 0.03 at % of Ir and 0.02 at % of Ru in combination were added to a ternary alloy of Ag—Pd—Cu consisting of 17 at % to 25 at % (21.20 at %) of Ag, 30 at % to 45 at % (38.40 at %) of Pd, and 30 at % to 53 at % (36.35 at %) of Cu in the atomic ratio.

In Comparative Example 15, the composition is that the 3.5 at % of Mn and 2 at % of Sn in combination were added to a ternary alloy of Ag—Pd—Cu consisting of 17 at % to 25 at % (20.00 at %) of Ag, 30 at % to 45 at % (35.50 at %) of Pd, and 30 at % to 53 at % (40.00 at %) of Cu in the atomic ratio.

In Comparative Example 16, the composition is that 1 at % of indium (In) and 0.05 at % of Ir were added to a ternary alloy of Ag—Pd—Cu consisting of 17 at % to 25 at % (24.35 at %) of Ag, 30 at % to 45 at % (33.05 at %) of Pd, and 30 at % to 53 at % (41.55 at %) of Cu in the atomic ratio.

In Comparative Example 17, the composition is that the 3.5 at % of Mn and 1 at % of In in combination were added, and 0.05 at % of Ir was added, to a ternary alloy of Ag—Pd—Cu consisting of 17 at % to 25 at % (20.00 at %) of Ag, 30 at % to 45 at % (35.50 at %) of Pd, and 30 at % to 53 at % (39.95 at %) of Cu in the atomic ratio.

Hereinafter, measurement results of Examples 1 to 32 and Comparative Examples 1 to 17 will be explained. In Example 1, it was confirmed that the Vickers hardness after aging treatment was HV 480 or more (HV 543). Further, the Vickers hardness after aging treatment was harder as compared with that in Comparative Examples 1 to 6 in which the composition is that Mn is not added to a ternary alloy of Ag—Pd—Cu, and it was confirmed that the Vickers hardness had been improved. In addition, in Comparative Example 6, the composition is outside the range of 17 at % to 25 at % of Ag, 30 at % to 45 at % of Pd, and 30 at % to 53 at % of Cu, respectively, and it was confirmed that the hardness is particularly lower as compared with that in Comparative Examples 1 to 5. However, in Comparative Examples 1 to 6, the hardening had not sufficiently proceeded in one hour, therefore, the heating at 400° C. was performed for 2 hours, the resultant was cut off, and the hardness after aging treatment was measured.

Further, as compared with Comparative Example 7 in which the composition is that 3.5 at % of Mn was added to a ternary alloy of Ag—Pd—Cu, the ternary alloy was in a range of 17 at % to 25 at % of Ag, 30 at % to 45 at % of Pd, and 30 at % to 53 at % of Cu, and it was confirmed that the Vickers hardness after aging treatment had been improved. In addition, in Comparative Example 9, it was confirmed that in spite of the composition range of the Ag—Pd—Cu ternary alloy described above, by the addition of 4.0 at % of Mn, conversely the age hardening hardly occurs, the improvement of Vickers hardness is not recognized, and further the workability is also deteriorated.

In Examples 2 to 13, the composition is that 0.5 at % to 3.5 at % of Mn was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 2 to 13, the Vickers hardness after aging treatment was HV 487 to 554, and the workability was also favorable. From these results, it was confirmed that as compared with Comparative Examples 1 to 5 in which Mn, Ir, or Ru had not been added, the addition of Mn, Ir, or Ru is involved in the improvement of Vickers hardness.

Figure 6:
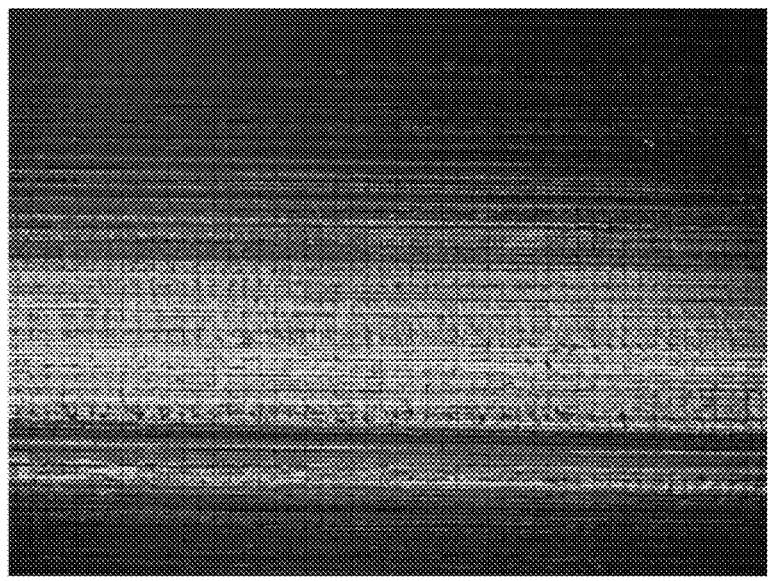
FIG. 6 is a picture illustrating an alloy material according to Examples of the present invention.

FIG. 6 is a picture illustrating an alloy material according to Example 8 of the present invention, and a picture of a surface of the alloy having a working rate of 84% and φ2.0 mm. As illustrated in FIG. 6, the alloy material was favorable without having no fine cracks on the surface thereof.

In Examples 14 to 16, the composition is that 1 at % to 2 at % of Sn was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 14 to 16, the Vickers hardness after aging treatment was HV 506 to 553, and the workability was favorable. From these results, it was confirmed that as compared with Comparative Examples 1 to 5 in which Sn had not been added, the addition of Sn is involved in the improvement of Vickers hardness.

On the contrary, in Comparative Example 8, although Sn had been added, the composition is outside the composition range of 17 at % to 25 at % of Ag, 30 at % to 45 at % of Pd, and 30 at % to 53 at % of Cu described above in a ternary alloy of Ag—Pd—Cu, and it was confirmed that the improvement of Vickers hardness is not recognized in this composition.

Further, in Comparative Example 10, the composition is that 3 at % (>2 at %) of Sn was added to a ternary alloy of Ag—Pd—Cu in the composition range according to the present embodiment, and it was confirmed that the improvement of hardness was obtained, however, the workability was deteriorated.

In Examples 17 and 18, the composition is that 0.5 at % to 2 at % of Si was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 17 and 18, the Vickers hardness after aging treatment was HV 523 and HV 494, and the workability was also favorable. From these results, it was confirmed that as compared with Comparative Examples 1 to 5, the addition of Si is involved in the improvement of Vickers hardness.

On the contrary, in Comparative Example 11, the composition is that 3 at % (>2 at %) of Si was added to a ternary alloy of Ag—Pd—Cu in the composition range according to the present embodiment, and it was confirmed that the improvement of hardness was obtained, however, the workability was deteriorated.

In Examples 19 and 20, the composition is that 0.5 at % to 3 at % of Sb was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 19 and 20, the Vickers hardness after aging treatment was HV 512 and HV 524, and the workability was also favorable. From these results, it was confirmed that as compared with Comparative Examples 1 to 5, the addition of Sb is involved in the improvement of Vickers hardness.

On the contrary, in Comparative Example 12, it was confirmed that in spite of the composition range of the ternary alloy of Ag—Pd—Cu described above, by the addition of 4 at % (>3 at %) of Sb, conversely the age hardening hardly occurs, and the workability is deteriorated.

In Examples 21 and 22, the composition is that 0.5 at % to 2 at % of Ti was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 21 and 22, the Vickers hardness after aging treatment was HV 515 and HV 526, and the workability was also favorable. From these results, it was confirmed that as compared with Comparative Examples 1 to 5, the addition of Ti is involved in the improvement of Vickers hardness.

On the contrary, in Comparative Example 13, it was confirmed that in spite of the composition range of the ternary alloy of Ag—Pd—Cu described above, by the addition of 3 at % (>2 at %) of Ti, conversely the age hardening hardly occurs, and further the workability is deteriorated.

In Examples 23 and 24, the composition is that 0.5 at % to 3.5 at % of Mg was added, and 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 23 and 24, the Vickers hardness after aging treatment was HV 511 and HV 523, and the workability was also favorable. From these results, it was confirmed that as compared with Comparative Examples 1 to 5, the addition of Mg is involved in the improvement of Vickers hardness.

On the contrary, in Comparative Example 14, it was confirmed that in spite of the composition range of the ternary alloy of Ag—Pd—Cu described above, by the addition of 4 at % (>3.5 at %) of Mg, conversely the age hardening hardly occurs, and further the workability is deteriorated.

In Examples 25 to 32, the composition is that at least one of Mn, Sn, Si, Sb, Ti, and Mg is added in a range of 4.5 at % or less, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at %, respectively, and further 0.01 at % to 0.05 at % of one of Ir and Ru or the Ir and Ru in combination were added based on the ternary alloy of Ag—Pd—Cu consisting of 17 at % to 25 at % of Ag, 30 at % to 45 at % of Pd, and 30 at % to 53 at % of Cu in the atomic ratio. In Examples 25 to 32, the Vickers hardness after aging treatment was HV 523 to 530, and the workability was also favorable. From these results, it was confirmed that as compared with Comparative Examples 1 to 5, the addition of the Mn, Sn, Si, Sb, Ti, and Mg in combination is involved in the improvement of Vickers hardness.

On the contrary, in Comparative Example 15, the composition is that the 3.5 at % of Mn and 2 at % of Sn in combination were added based on the ternary alloy of Ag—Pd—Cu in the composition range according to the present embodiment. In Example 15, as compared with Examples 25 to 32, the Vickers hardness was not changed, however, the workability was deteriorated. From these results, it was confirmed that in a case where the Mn, Sn, Si, Sb, Ti, and Mg in combination are 4.5 at % or more, the workability is deteriorated, and the material is not preferable as an alloy material.

Further, in Comparative Example 16, 1 at % of In and 0.05 at % of Ir were added based on the ternary alloy of Ag—Pd—Cu in the composition range according to the present embodiment. Further, in Comparative Example 16, the Vickers hardness was HV 470, and as compared with Comparative Examples 1 to 5, the improvement of hardness was obtained, however, as compared with the composition in Example 10 in which 1 at % of Mn was added, or the composition in Example 16 in which 1 at % of Sn was added, which is a similar composition, the improvement of hardness is small. Further, in Comparative Example 16, as compared with Examples 17, 19, 21, and 23 in which the composition is that 0.5 at % of any of Si, Sb, Ti, and Mg were added in combination, which is a similar composition, the improvement of hardness is small.

Further, in Comparative Example 17, the composition is that the 3.5 at % of Mn and 1 at % of In in combination were added, and 0.05 at % of Ir was added, based on the ternary alloy of Ag—Pd—Cu in the composition range according to the present embodiment. In Comparative Example 17, as compared with the independent addition or combination addition of Mn, Sn, Si, Sb, Ti, and Mg, the hardness is not largely changed, and the workability is slightly deteriorated. As a result, the Vickers hardness according to the difference of the additional metal to the ternary alloy of Ag—Pd—Cu consisting of 17 at % to 25 at % of Ag, 30 at % to 45 at % of Pd, and 30 at % to 53 at % of Cu was confirmed to be more effective in Mn, Sn, Si, Sb, Ti, and Mg than in In.

Figure 7:
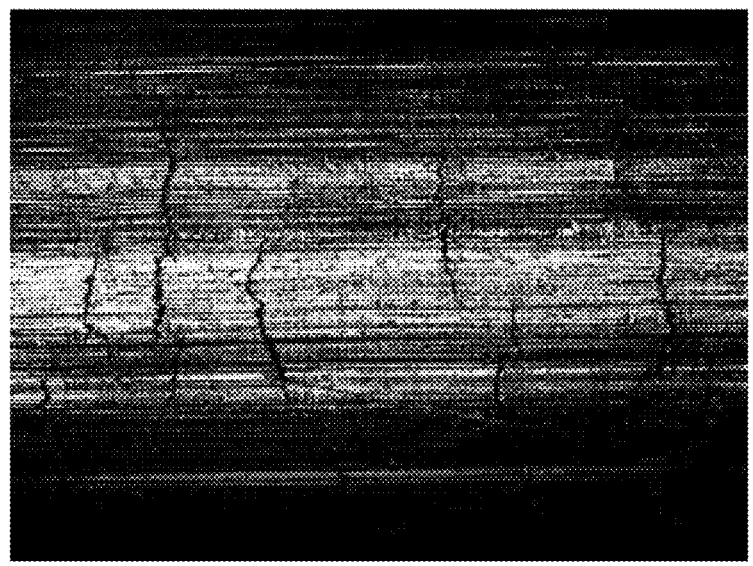
FIG. 7 is a picture illustrating an alloy material according to Comparative Examples of the present invention.

FIG. 7 is a picture illustrating an alloy material according to Comparative Example 17 of the present invention, and a picture of a surface of the alloy having a working rate of 84% and φ2.0 mm. As illustrated in FIG. 7, fine cracks were observed on the surface of the alloy material.

In addition, in Examples 1 to 32 and Comparative Examples 1 to 17 described above, the explanation was performed as the one treated at a temperature of aging treatment of 400° C., and in the composition of Example 7, the hardness, electric conductivity, and workability obtained by the aging treatment at a temperature of 300° C. (Example 7-1), 350° C. (Example 7-2), or 450° C. (Example 7-3) are shown in Table 1. Further, in an alloy material in which the additional metals are the same as those in Examples 7-1 to 7-3 (the 3.5 at % of Mn and 0.05 at % of Ir in combination were added based on the ternary alloy of Ag—Pd—Cu in the composition range according to the present embodiment), the hardness, electric conductivity, and workability obtained by the aging treatment at a temperature of 275° C. (Comparative Example 18-1), or 475° C. (Comparative Example 18-2), are shown in Table 2.

In Examples 7-1, 7-2, and 7-3, the Vickers hardness after aging treatment was HV 481 to 541, and the workability was also favorable. From these results, it was confirmed that even if the temperature of the aging treatment is 300° C., 350° C., or 450° C., an alloy material having a favorable Vickers hardness is obtained. On the other hand, in Comparative Examples 18-1 and 18-2, the Vickers hardness after aging treatment was HV 380 and HV 401. From these results, if the temperature of the aging treatment is lower than 300° C., or higher than 450° C., an alloy material having a favorable Vickers hardness is not obtained.

Further, in the measurement of electric conductivity, in the above-described Examples 1 to 32, and Examples 7-1, 7-2, and 7-3, it was confirmed that the conductivity is favorable.

In addition, in Example 1, Examples 3 to 10, Examples 15 to 17, and Examples 19 to 32, the composition is that based on each composition of 18 at % Ag-35 at % Pd-47 at % Cu, 22 at % Ag-35 at % Pd-43 at % Cu, 18 at % Ag-40 at % Pd-42 at % Cu, and 22 at % Ag-40 at % Pd-38 at % Cu in the composition range described above, at least one of Mn, Sn, Si, Sb, Ti and Mg is added in a range of 4.5 at % or less, in which the Mn is in a range of 0.5 at % to 3.5 at %, the Sn is in a range of 1 at % to 2 at %, the Si is in a range of 0.5 at % to 2 at %, the Sb is in a range of 0.5 at % to 3 at %, the Ti is in a range of 0.5 at % to 2 at %, and the Mg is in a range of 0.5 at % to 3.5 at %, respectively. In Example 1, Examples 3 to 10, Examples 15 to 17, and Examples 19 to 32, the improvement of Vickers hardness is larger as compared with that in Example 2, Examples 11 to 14, and Example 18, therefore, it is more preferable to use a ternary alloy of Ag—Pd—Cu in this composition range in order to obtain the maximum hardness.

INDUSTRIAL APPLICABILITY

As described above, an alloy material according to the present invention, and a contact probe and a connection terminal each of which consists of the alloy material, are useful as a contact probe in terms of conductivity, hardness, and workability.

REFERENCE SIGNS LIST

1 Socket
2, 2a Contact probe (probe)

3 Probe holder
4 Holder member
5 Probe card
6 Connector pedestal
21, 24 First plunger
21a, 21f, 22a End portion
21b Pawl portion
21c, 22b Flange portion
21d, 22c Boss part
21e, 22d Proximal end portion
22 Second plunger
23 Coil spring
23a Tightly wound coil part
23b Roughly wound coil part
31 First member
32 Second member
33, 34 Holder hole
33a, 34a Small diameter part
33b, 34b Large diameter part
51 Substrate
52 Reinforcing member
53 Interposer
54 Space transformer
55 Probe head
56 Holding member
57 Leaf spring
58 Wiring
59 Male connector
60 Female connector
70 Wafer chuck
100 Semiconductor integrated circuit
100a Semiconductor wafer
101, 101a Connection electrode
200 Circuit board
201 Electrode
541 Electrode pad

The invention claimed is:

1. An alloy material, consisting of:
   a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and
   at least one of manganese (Mn), tin (Sn), silicon (Si), antimony (Sb), titanium (Ti) and magnesium (Mg) added to the composition in a range of 4.5 at % or less,
   wherein the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition, and
   one of iridium (Ir), ruthenium (Ru) and a combination of Ir and Ru is further added in an amount of 0.01 at % to 0.05 at %.

2. The alloy material according to claim 1, wherein Vickers hardness is HV 480 to 560 after heating at 300° C. to 450° C. and aging.

3. A conductive contact probe contacting with each of contact targets at both ends in a longitudinal direction,
   at least part of which is formed using an alloy material, consisting of:
   a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and
   at least one of manganese (Mn), tin (Sn), silicon (Si), antimony (Sb), titanium (Ti) and magnesium (Mg) added to the composition in a range of 4.5 at % or less,
   wherein the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition, and
   one of iridium (Ir), ruthenium (Ru) and a combination of Ir and Ru is further added in an amount of 0.01 at % to 0.05 at %.

4. The conductive contact probe according to claim 3, consisting of:
   a first conductive plunger contacting with one of contact targets at one end;
   a second conductive plunger contacting with other one of the contact targets at the other end; and
   a coil spring arranged between the first plunger and the second plunger so as to elastically connect the first and the second plungers with each other,
   wherein at least one of the first plunger, the second plunger, and the coil spring consists of the alloy material.

5. The conductive contact probe according to claim 4, wherein Vickers hardness is HV 480 to 560 after heating at 300° C. to 450° C. and aging.

6. The conductive contact probe according to claim 3, wherein Vickers hardness is HV 480 to 560 after heating at 300° C. to 450° C. and aging.

7. A conductive connection terminal contacting with each of contact targets at both ends in a longitudinal direction,
   at least part of which is formed using an alloy material, consisting of:
   a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and
   at least one of manganese (Mn), tin (Sn), silicon (Si), antimony (Sb), titanium (Ti) and magnesium (Mg) added to the composition in a range of 4.5 at % or less,
   wherein the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition, and
   one of iridium (Ir), ruthenium (Ru) and a combination of Ir and Ru is further added in an amount of 0.01 at % to 0.05 at %.

8. The conductive connection terminal according to claim 7, wherein Vickers hardness is HV 480 to 560 after heating at 300° C. to 450° C. and aging.

9. A conductive contact probe contacting with each of contact targets at both ends in a longitudinal direction,
   at least part of which is formed using an alloy material, comprising:
   a composition containing 17 at % to 25 at % of silver (Ag), 30 at % to 45 at % of palladium (Pd), and 30 at % to 53 at % of copper (Cu) in a composition range of a ternary alloy of Ag, Pd, and Cu; and
   at least one of manganese (Mn), tin (Sn), silicon (Si), antimony (Sb), titanium (Ti) and magnesium (Mg) added to the composition in a range of 4.5 at % or less,
   wherein the Mn in a range of 0.5 at % to 3.5 at %, the Sn in a range of 1 at % to 2 at %, the Si in a range of 0.5 at % to 2 at %, the Sb in a range of 0.5 at % to 3 at %, the Ti in a range of 0.5 at % to 2 at %, and the Mg in a range of 0.5 at % to 3.5 at % are added to the composition, and one of iridium (Ir), ruthenium (Ru) and a combination of Ir and Ru is further added in an amount of 0.01 at % to 0.05 at %, and the conductive contact probe, comprising:
  a first conductive plunger contacting with one of contact targets at one end;
  a second conductive plunger contacting with other one of the contact targets at the other end; and
  a coil spring arranged between the first plunger and the second plunger so as to elastically connect the first and the second plungers with each other,
  wherein at least one of the first plunger, the second plunger, and the coil spring consists of the alloy material.

10. The conductive contact probe according to claim 9, wherein Vickers hardness is HV 480 to 560 after heating at 300° C. to 450° C. and aging.

\* \* \* \* \*